(12) United States Patent
Schelberger et al.

(10) Patent No.: US 6,369,090 B1
(45) Date of Patent: Apr. 9, 2002

(54) FUNGICIDAL MIXTURE

(75) Inventors: Klaus Schelberger, Gönnheim; Reinhold Saur, Böhl-Iggelheim; Hubert Sauter, Mannheim; Bernd Müller, Frankenthal; Erich Birner, Altleiningen; Joachim Leyendecker, Hassloch; Manfred Hampel, Neustadt; Eberhard Ammermann, Heppenheim; Gisela Lorenz, Neustadt; Siegfried Strathmann, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/424,916
(22) PCT Filed: May 20, 1998
(86) PCT No.: PCT/EP98/02946
  § 371 Date: Dec. 1, 1999
  § 102(e) Date: Dec. 1, 1999
(87) PCT Pub. No.: WO98/54969
  PCT Pub. Date: Dec. 10, 1998

(30) Foreign Application Priority Data

Jun. 4, 1997 (DE) ............................. 197 23 281

(51) Int. Cl.[7] .................. A01N 43/64; A01N 37/18; A01N 43/40; A01N 43/54; A61K 31/535
(52) U.S. Cl. ................. 514/384; 514/63; 514/231.2; 514/239.5; 514/260; 514/317; 514/383; 514/407; 514/619
(58) Field of Search ................... 514/407, 384, 514/619, 239.5, 231.2, 317, 383, 260, 63

(56) References Cited

U.S. PATENT DOCUMENTS

| | | | |
|---|---|---|---|
| 5,106,848 A | 4/1992 | Seele et al. | 514/239 |
| 5,395,854 A | 3/1995 | Brand et al. | 514/619 |
| 5,472,963 A | * 12/1995 | Wingert et al. | 514/239.5 |
| 5,476,868 A | * 12/1995 | Wingert et al. | 514/383 |

FOREIGN PATENT DOCUMENTS

| | | |
|---|---|---|
| AU | 63760/94 | 10/1994 |
| DE | 43 43 176 | 6/1995 |
| EP | 477 631 | 4/1992 |
| EP | 0645 087 | 3/1995 |
| EP | 0737 421 | 10/1996 |
| WO | 96/01256 | 1/1996 |
| WO | 96/01258 | 1/1996 |
| WO | 97/06686 | 2/1997 |
| WO | 97/39865 | 10/1997 |
| WO | 97/40673 | 11/1997 |
| WO | 97/40674 | 11/1997 |
| WO | 97/40688 | 11/1997 |

\* cited by examiner

*Primary Examiner*—Allen J. Robinson
(74) *Attorney, Agent, or Firm*—Keil & Weinkauf

(57) ABSTRACT

Fungicidal mixtures comprise a.1) a carbamate of the formula I.a,

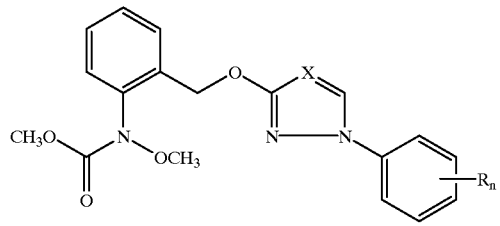

I.a in which X is CH or N, n is 0, 1 or 2 and R is halogen, alkyl or haloalkyl, or a.2) the oxime ether carboxamide of the formula I.b

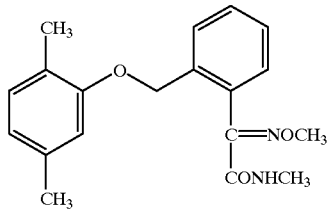

I.b and b.1) 4-[2-methyl-3-(4-tert-butylphenyl)propyl]-2,6-dimethyl morpholine

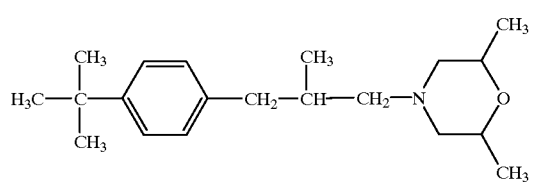

II.a or b.2) 4-($C_{10}$–$C_{13}$-alkyl)-2,6-dimethylmorpholine

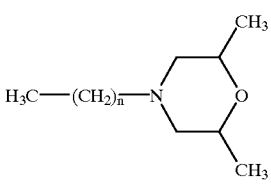

II.b

[n = 10, 11, 12 (60–70%), 13]

or
b.3) (RS)-1-[3-(4-tert-butylphenyl)-2-methylpropyl]piperidine
II.c
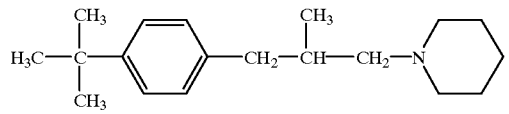
and
c) an active ingredient from the group of the azole fungicides (III),
in a synergistically effective amount.
20 Claims, No Drawings

FUNGICIDAL MIXTURE

This application is a 371 of PCT/EP98/02946, filed May 20, 1998.

The present invention relates to a fungicidal mixture which comprises a.1) a carbamate of the formula I.a,

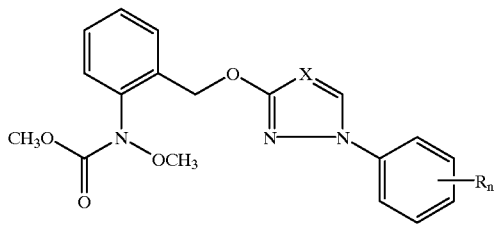

I.a in which X is CH or N, n is 0, 1 or 2 and R is halogen, $C_1$–$C_4$-alkyl or $C_1$–$C_4$-haloalkyl, it being possible for the radicals R to be different if n is 2, or a.2) the oxime ether carboxamide of the formula I.b

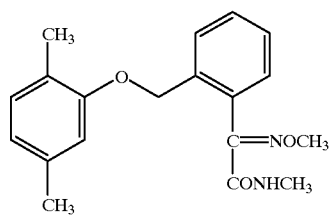

I.b and b.1) 4-[2-methyl-3-(4-tert-butylphenyl)propyl]-2,6-dimethylmorpholine

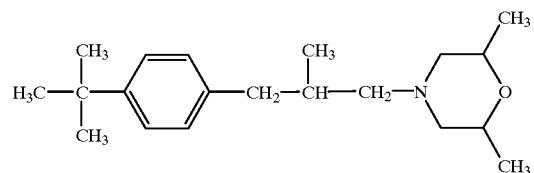

II.a or b.2) 4-($C_{10}$–$C_{13}$-alkyl)-2,6-dimethylmorpholine

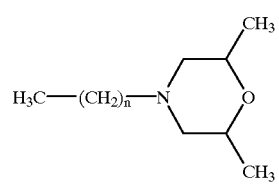

II.b

[n = 10, 11, 12 (60–70%), 13]

or b.3) (RS)-1-[3-(4-tert-butylphenyl)-2-methylpropyl] piperidine

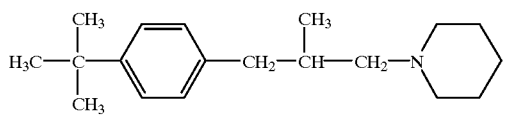

II.c and c) an active ingredient from the group of the azole fungicides (III), in a synergistically effective amount.

Particular preference is given to mixtures in which one of the compounds III.1 to III.33 serves as azole fungicide:

III.1  1-{[2-(2,4-dichlorophenyl)-1,3-dioxolan-2-yl]-1H-1,2,4-triazole

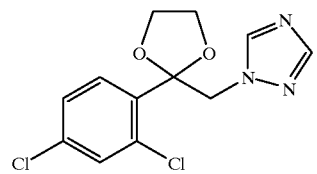

III.1

III.2  1-(biphenyl-4-yloxy)-3,3-dimethyl-1-(1H-1,2,4-triazol-1-yl)butan-2-ol

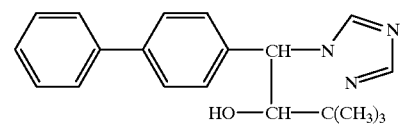

III.2

III.3  1-[(2RS, 4RS; 2RS, 4SR)-4-bromo-2-(2,4-dichlorophenyl)tetrahydrofurfuryl]-1H-1,2,4-triazole

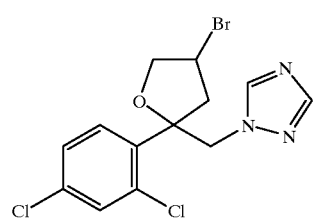

III.3

III.4  (2RS, 3RS, 2RS, 3SR)-2-(4-chlorophenyl)-3-cyclopropyl-1-(1H-1,2,4-triazol-1-yl)butan-2-ol

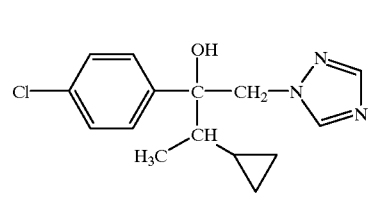

III.4

III.5 (2RS, 3RS)-1-(2,4-dichlorophenyl)-4,4-dimethyl-2-(1H-1,2,4-triazol-1-yl)pentan-3-ol

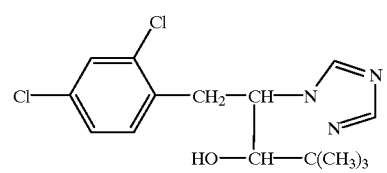

III.5

III.6 cis, trans-3-chloro-4-[4-methyl-2-(1H-1,2,4-triazol-1-ylmethyl)-1,3-dioxolan-2-yl]phenyl 4-chlorophenyl ether

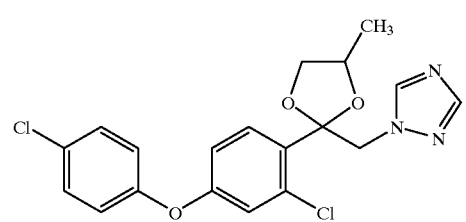

III.6

III.7 (E)-(R,S)-1-(2,4-dichlorophenyl)-4,4-dimethyl-2-(1H-1,2,4-triazol-1-yl)pent-1-en-3-ol

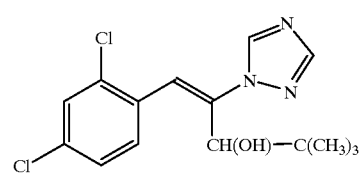

III.7

III.8 (2RS, 3RS)-1-[3-(2-chlorophenyl)-2,3-epoxy-2-(4-fluorophenyl)propyl]-1H-1,2,4-triazole

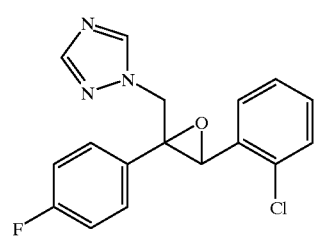

III.8

III.9 (±)-1-[2-(2,4-dichlorophenyl)-4-ethyl-1,3-dioxolan-2-ylmethyl]-1H-1,2,4-triazole

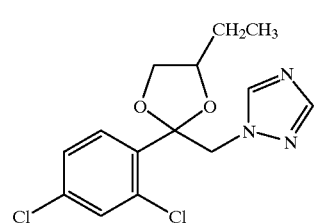

III.9

III.10 (RS) -4-(4-chlorophenyl)-2-phenyl-2-(1H-1,2,4-triazol-1-ylmethyl)butyronitrile

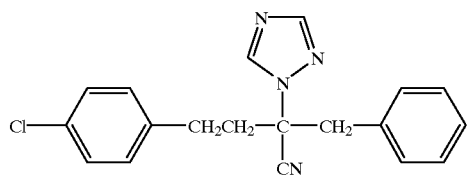

III.10

III.11 3-(2,4-dichlorophenyl)-6-fluoro-2-(1H-1,2,4-triazol-1-yl)quinazolin-4(3H)-one

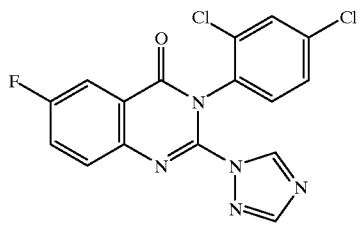

III.11

III.12 bis-(4-fluorophenyl)(methyl)-(1H-1,2,4-triazol-1-ylmethyl)silane

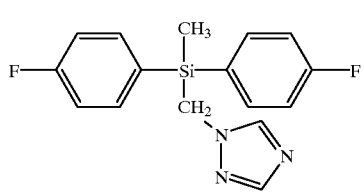

III.12

III.13 (RS)-2,4'-difluoro-α-(1H-1,2,4-triazol-1-ylmethyl) benzhydryl alcohol

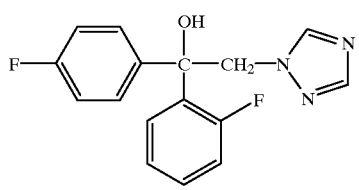

III.13

III.14 (RS)-2-(2,4-dichlorophenyl)-1-(1H-1,2,4-triazol-1-yl)-hexan-2-ol

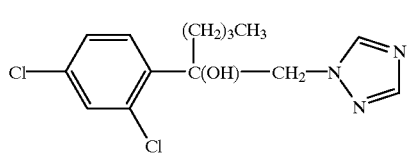

III.14

III.15 (1)-1-(β-allyloxy-2,4-dichlorophenylethyl) imidazole

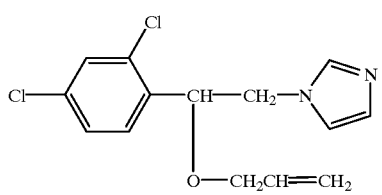

III.16 4-chlorobenzyl N-(2,4-dichlorophenyl)-2-(1H-1,2,4-triazol-1-yl)thioacetamidate

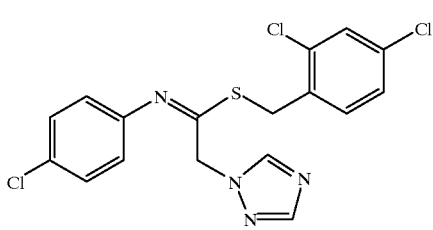

III.17 (1RS,2SR,5RS; 1RS,2SR,5SR) -2-(4-chlorobenzyl)-5-isopropyl-1-(1H-1,2,4-triazol-1-ylmethyl)cyclopentanol

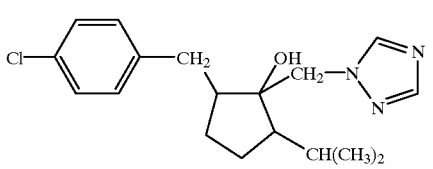

III.18 (1RS,5RS; 1RS,5SR)-5-(4-chlorobenzyl)-2,2-dimethyl-1-(1H-1,2,4-triazol-1-ylmethyl)cyclopentanol

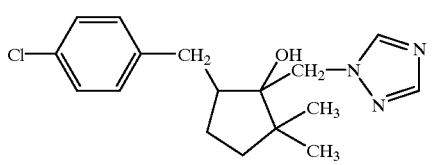

III.19 2-(4-chlorophenyl)-2-cyano-1-(1H-1,2,4-triazol-1-yl)-hexane

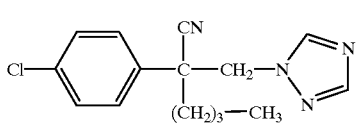

III.20 2-(4-chlorophenyl)-3-hydroxy-4,4-dimethyl-1-(1H-1,2,4-triazol-1-yl)pentane

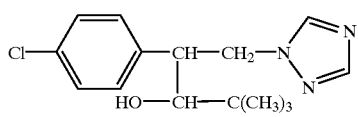

III.21 pent-4-enyl N-furfuryl-N-imidazol-1-ylcarbonyl-DL-homoalaninate

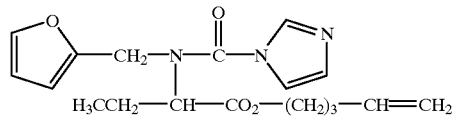

III.22 2-(2,4-dichlorophenyl)-1-(1H-1,2,4-triazol-1-yl)pentane

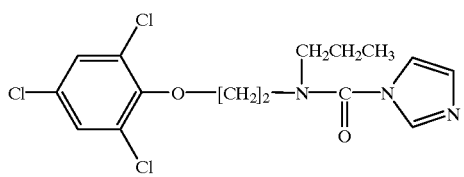

III.23 N-propyl-N-[(2,4,6-trichlorophenoxy)ethyl]imidazole-1-carboxamide

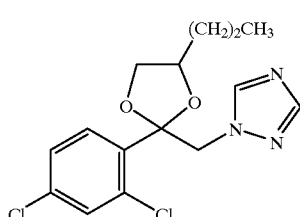

III.24 (±)-1-{[2-(2,4-dichlorophenyl)-4-propyl-1,3-dioxolan-2-yl]methyl}-1H-1,2,4-triazole

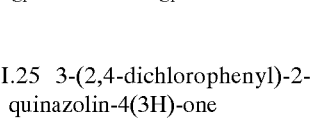

III.25 3-(2,4-dichlorophenyl)-2-(1H-1,2,4-triazol-1-yl)quinazolin-4(3H)-one

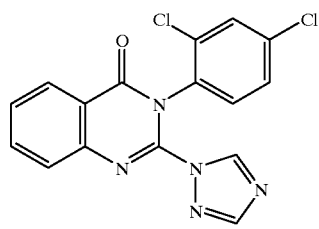

III.25

III.26 (±)-cis)-1-(4-chlorophenyl)-2-(1H-1,2,4-triazol-1-yl)cycloheptanol

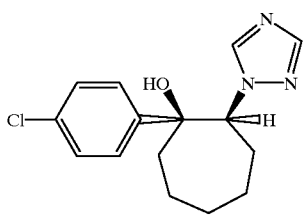

III.26

III.27 1-(4-chlorophenyl)-4,4-dimethyl-3-(1H-1,2,4-triazol-1yl)pentan-3-ol

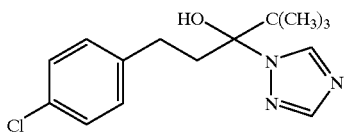

III.27

III.28 (RS)-2-(2,4-dichlorophenyl)-3-(1H-1,2,4-triazol-1-yl)propyl 1,1,2,2-tetrafluoroethyl ether

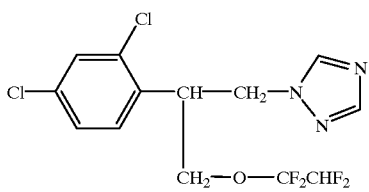

III.28

III.29 1-(4-chlorophenoxy)-3,3-dimethyl-1-(1H-1,2,4-triazol-1-yl)butan-2-one

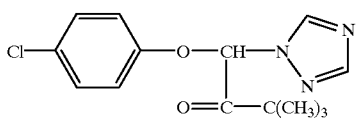

III.29

III.30 (1RS,2RS; 1RS,2SR) 1-(4-chlorophenoxy)-3,3-dimethyl-1-(1H-1,2,4-triazol-1-yl)butan-2-ol

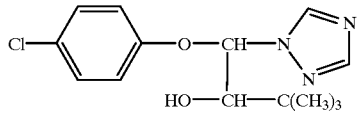

III.30

III.31 (E)-4-chloro-α,α,α-trifluoro-N-(1-imidazol-1-yl-2-propoxyethylidene)-o-toluidine

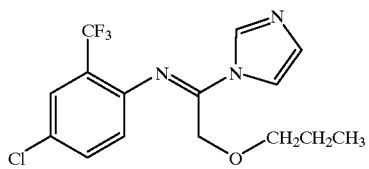

III.31

III.32 (±)-(E)-5-(4-chlorobenzylidene)-2,2-dimethyl-1-(1H-1,2,4-triazol-1-ylmethyl)cyclopentanol

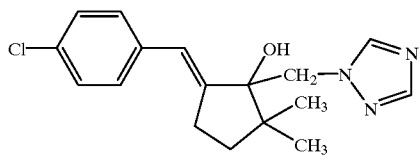

III.32

III.33 (E)-(RS)-1-(4-chlorophenyl)-4,4-dimethyl-2-(1H-1,2,4-triazol-1-yl)pent-1-en-3-ol

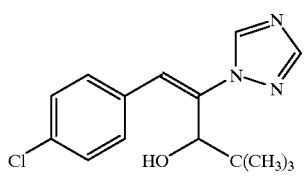

III.33

Moreover, the invention relates to methods for controlling harmful fungi using mixtures of the compounds I (I.a and I.b), II (II.a, II.b and II.c) and III (III.1–III.33).

The compounds of the formula I, their preparation and their activity against harmful fungi are disclosed in the literature (EP-A 477 631; WO-A 96/01,256; WO-A 96/01, 258).

Also known are the compounds of the formula II:

II.a (common name: fenpropimorph): CAS RN [67564-91-4], U.S. Pat. No. 4,202,894;

II.b (common name: tridemorph): CAS RN [81412-43-3], DE-A 11 64 152;

II.c (common name: fenpropidin): CAS RN [67306-00-7], U.S. Pat. No. 4,202,894.

In addition, the compounds III are described in the literature as active compounds for controlling harmful fungi:

III.1 (common name: azaconazole): CAS RN [60207-31-0];

III.2 (common name: biteranol): CAS RN [70585-36-3], DE-A 23 24 010;

III.3 (common name: bromuconazole): CAS RN [116255-48-2];

III.4 (common name: cyproconazole): CAS RN [94361-06-5], U.S. Pat. No. 4,664,696;

III.5 (common name: diclobutrazol): CAS RN [75736-33-3];

III.6 (common name: difenconazole): CAS RN [119446-68-3], EP-A 65 485;

III.7 (common name: diniconazole): CAS RN [83657-24-3];

III.8 (proposed common name: epoxiconazole): CAS RN [106325-08-0];

III.9 (common name: etaconazole): CAS RN [60207-93-4];

III.10 (common name: fenbuconazole): CAS RN [114369-43-6];

III.11 (common name: fluquinconazole): CAS RN [136426-54-5];

III.12 (common name: flusilazole): CAS RN [85509-19-9];

III.13 (common name: flutriafol): CAS RN [76674-21-0], EP-A 15 756;

III.14 (common name: hexaconazole): CAS RN [79983-71-4];

III.15 (common name: imazalil): CAS RN [73790-28-0];

III.16 (common name: imibenzconazole): CAS RN [86598-92-7];

III.17 (common name: ipconazole): CAS RN [125225-28-7], EP-A 267 778;

III.18 (common name: metconazole): CAS RN [125116-23-6];

III.19 (common name: myclobutanil): CAS RN [88671-89-0];

III.20 (common name: paclobutrazol): CAS RN [76738-62-0], U.S. Pat. No. 1,595,697;

III.21 (common name: pefurazoate): CAS RN [101903-30-4];

III.22 (common name: penconazole): CAS RN [66246-88-6], GB-A 1 589 852;

III.23 (common name: prochloraz): CAS RN [67747-09-5], U.S. Pat. No. 4,080,462;

III.24 (common name: propiconazole): CAS RN [60207-90-1], GB-A 1 522 657;

III.25 (common name: quinconazole): CAS RN [103970-75-8];

III.26 (code name: SSF 109): CAS RN [129586-32-9];

III.27 (common name: tebuconazole): CAS RN [107534-96-3], EP-A 40 345;

III.28 (common name: tetraconazole): CAS RN [112281-77-3], EP-A 234 242;

III.29 (common name: triadimefon): CAS RN [43121-43-3], U.S. Pat. No. 3,912,752;

III.30 (common name: triadimenol): CAS RN [55219-65-3], DE-A 23 24 010;

III.31 (common name: triflumizole): CAS RN [99387-89-0], JP-A 79/119,462;

III.32 (common name: triticonazole): CAS RN [131983-72-7];

III.33 (common name: uniconazole): CAS RN [83657-22-1].

Synergistic mixtures of the compounds I.a with active compounds II.a to II.c are described in the earlier application DE P 19 616 724.8, and synergistic mixtures of the compounds I.a with active compounds III.1 to III.33 are described in the earlier application DE P 19 618 676.5.

Moreover, EP-A 645 087 discloses synergistic mixtures of the compound I.b with the active compounds II.a to II.c, and EP-A 645 091 discloses synergistic mixtures of the compound I.b with some of the active compounds III.1 to III.33.

It is an object of the present invention to provide mixtures which have an improved activity against harmful fungi combined with a reduced total amount of active ingredients applied (synergistic mixtures), with a view to reducing the application rates and to improving the activity spectrum of the known compounds I, II and III.

We have found that this object is achieved by the mixture defined at the outset. Moreover, we have found that better control of harmful fungi is possible by applying the compounds I, II and III simultaneously, that is either together or separately, or by applying the compounds I, II and III in succession than when the individual compounds are used.

The formula I.a represents in particular carbamates in which the combination of the substituents corresponds to a row of the following Table:

I.a

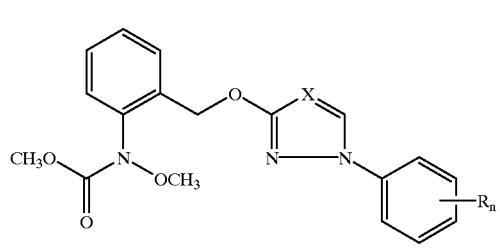

| No. | X | $R_n$ |
|---|---|---|
| Ia.1 | N | 2-F |
| Ia.2 | N | 3-F |
| Ia.3 | N | 4-F |
| Ia.4 | N | 2-Cl |
| Ia.5 | N | 3-Cl |
| Ia.6 | N | 4-Cl |
| Ia.7 | N | 2-Br |
| Ia.8 | N | 3-Br |
| Ia.9 | N | 4-Br |
| Ia.10 | N | 2-CH$_3$ |
| Ia.11 | N | 3-CH$_3$ |
| Ia.12 | N | 4-CH$_3$ |
| Ia.13 | N | 2-CH$_2$CH$_3$ |
| Ia.14 | N | 3-CH$_2$CH$_3$ |
| Ia.15 | N | 4-CH$_2$CH$_3$ |
| Ia.16 | N | 2-CH(CH$_3$)$_2$ |
| Ia.17 | N | 3-CH(CH$_3$)$_2$ |
| Ia.18 | N | 4-CH(CH$_3$)$_2$ |
| Ia.19 | N | 2-CF$_3$ |
| Ia.20 | N | 3-CF$_3$ |
| Ia.21 | N | 4-CF$_3$ |
| Ia.22 | N | 2,4-F$_2$ |
| Ia.23 | N | 2,4-Cl$_2$ |
| Ia.24 | N | 3,4-Cl$_2$ |
| Ia.25 | N | 2-Cl, 4-CH$_3$ |
| Ia.26 | N | 3-Cl, 4-CH$_3$ |
| Ia.27 | CH | 2-F |
| Ia.28 | CH | 3-F |
| Ia.29 | CH | 4-F |
| Ia.30 | CH | 2-Cl |
| Ia.31 | CH | 3-Cl |
| Ia.32 | CH | 4-Cl |
| Ia.33 | CH | 2-Br |
| Ia.34 | CH | 3-Br |
| Ia.35 | CH | 4-Br |
| Ia.36 | CH | 2-CH$_3$ |
| Ia.37 | CH | 3-CH$_3$ |

-continued

| No. | X | $R_n$ |
|---|---|---|
| Ia.38 | CH | 4-CH$_3$ |
| Ia.39 | CH | 2-CH$_2$CH$_3$ |
| Ia.40 | CH | 3-CH$_2$CH$_3$ |
| Ia.41 | CH | 4-CH$_2$CH$_3$ |
| Ia.42 | CH | 2-CH(CH$_3$)$_2$ |
| Ia.43 | CH | 3-CH(CH$_3$)$_2$ |
| Ia.44 | CH | 4-CH(CH$_3$)$_2$ |
| Ia.45 | CH | 2-CF$_3$ |
| Ia.46 | CH | 3-CF$_3$ |
| Ia.47 | CH | 4-CF$_3$ |
| Ia.48 | CH | 2,4-F$_2$ |
| Ia.49 | CH | 2,4-Cl$_2$ |
| Ia.50 | CH | 3,4-Cl$_2$ |
| Ia.51 | CH | 2-Cl, 4-CH$_3$ |
| Ia.52 | CH | 3-Cl, 4-CH$_3$ |

Particular preference is given to the compounds Ia.12, Ia.23, Ia.32 and Ia.38.

Owing to the basic character of their nitrogen atoms, the compounds I, II and III are capable of forming salts or adducts with inorganic or organic acids or with metal ions.

Examples of inorganic acids are hydrohalic acids such as hydrofluoric acid, hydrochloric acid, hydrobromic acid and hydriodic acid, carbonic acid, sulfuric acid, phosphoric acid and nitric acid.

Suitable organic acids are, for example, formic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which carry one or two sulfo groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphoric acid radicals), it being possible for the alkyl or aryl radicals to carry further substituents, eg. p-toluenesulfonic acid, salicylic acid, p-aminosalicylic acid, 2-phenoxybenzoic acid, 2-acetoxybenzoic acid, etc.

Suitable metal ions are, in particular, the ions of the elements of the first to eighth sub-group, in particular chromium, manganese, iron, cobalt, nickel, copper, zinc and furthermore of the second main group, in particular calcium and magnesium, and of the third and fourth main group, in particular aluminum, tin and lead. The metals can exist in the various valencies which they can assume.

When preparing the mixtures, it is preferred to employ the pure active ingredients I, II and III, to which further active ingredients against harmful fungi or other pests, such as insects, arachnids or nematodes, or else herbicidal or growth-regulating active ingredients or fertilizers can be admixed.

The mixtures of the compounds I, II and III, or the simultaneous joint or separate use of the compounds I, II and III, exhibit, or provides, outstanding activity against a wide range of phytopathogenic fungi, in particular for the classes of the Ascomycetes, Basidiomycetes, Phycomycetes and Deuteromycetes.

Some of them act systemically and can therefore be employed as foliar- and soil-acting fungicides.

They are especially important for controlling a large number of fungi in a variety of crop plants, such as cotton, vegetable species (eg. cucumbers, beans, tomatoes, potatoes and cucurbits), barley, grass, oats, bananas, coffee, maize, fruit species, rice, rye, soja, grapevine, wheat, ornamentals, sugar cane, and a variety of seeds.

They are particularly suitable for controlling the following phytopathogenic fungi: Erysiphe graminis (powdery mildew) in cereals, Erysiphe cichoracearum and Sphaerotheca fuliginea in cucurbits, Podosphaera leucotricha in apples, Uncinula necator in grapevines, Puccinia species in cereals, Rhizoctonia species in cotton, rice and lawns, Ustilago species in cereals and sugar cane, Venturia inaequalis (scab) in apples, Helminthosporium species in cereals, Septoria nodorum in wheat, Botrytis cinerea (gray mold) in strawberries, vegetables, ornamentals and grapevines, Cercospora arachidicola in groundnuts, Pseudocercosporella herpotrichoides in wheat and barley, Pyricularia oryzae in rice, Phytophthora infestans in potatoes and tomatoes, Plasmopara viticola in grapevines, Pseudoperonospora species in hops and cucumbers, Alternaria species in vegetables and fruit, Mycosphaerella species in bananas and Fusarium and Verticillium species.

Furthermore, they can be used in the protection of materials (eg. in the protection of wood), for example against Paecilomyces variotii.

The compounds I, II and III can be applied simultaneously, either together or separately, or in succession, the sequence, in the case of separate application, generally not having any effect on the result of the control measures.

The compounds I and II are usually used in a weight ratio of 10:1 to 0.01:1, preferably 5:1 to 0.05:1, in particular 1:1 to 0.05:1.

The compounds I and III are usually used in a weight ratio of 10:1 to 0.01:1, preferably 5:1 to 0.05:1, in particular 1:1 to 0.05:1.

Depending on the kind of effect desired, the application rates of the mixtures according to the invention are, in particular in agricultural crops, from 0.01 to 8 kg/ha, preferably 0.1 to 5 kg/ha, in particular 0.2 to 3.0 kg/ha.

The application rates of the compounds I are from 0.01 to 2.5 kg/ha, preferably 0.05 to 2.5 kg/ha, in particular 0.1 to 1.0 kg/ha.

Correspondingly, in the case of the compounds II, the application rates are from 0.01 to 10 kg/ha, preferably 0.05 to 5 kg/ha, in particular 0.05 to 2.0 kg/ha.

Correspondingly, in the case of compounds III, the application rates are from 0.01 to 10 kg/ha, preferably 0.05 to 5 kg/ha, in particular 0.05 to 2.0 kg/ha.

For seed treatment, the application rates of the mixture are generally from 0.001 to 250 g/kg of seed, preferably 0.01 to 100 g/kg, in particular 0.01 to 50 g/kg.

If phytopathogenic harmful fungi are to be controlled, the separate or joint application of the compounds I, II and III or of the mixtures of the compounds I, II and III is effected by spraying or dusting the seeds, the plants or the soils before or after sowing of the plants, or before or after plant emergence.

The fungicidal synergistic mixtures according to the invention, or the compounds I, II and III, can be formulated for example in the form of ready-to-spray solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should guarantee as fine and uniform as possible a distribution of the mixture according to the invention.

The formulations are prepared in a manner known per se, eg. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or jointly grinding the compounds I, II and III, or the mixture of the compounds I, II and III with a solid carrier.

Granules (eg. coated granules, impregnated granules or homogeneous granules) are usually prepared by binding the active ingredient, or active ingredients, to a solid carrier.

Fillers or solid carriers are, for example, mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably 0.5 to 90% by weight, of one of the compounds I, II and III or of the mixture of the compounds I, II and III. The active ingredients are employed in a purity of from 90% to 100%, preferably 95% to 100% (according to NMR spectrum or HPLC).

The compounds I, II and III, or the mixtures, or the corresponding formulations, are applied by treating the harmful fungi, their habitat, or the plants, seeds, soils, areas, materials or spaces to be kept free from them with a fungicidally effective amount of the mixture, or of the compounds I, II and III in the case of separate application.

Application can be effected before or after infection by the harmful fungi.

USE EXAMPLES

The synergistic activity of the mixtures according to the invention was demonstrated by the following experiments:

The active ingredients, separately or together, were formulated as a 10% emulsion in a mixture of 63% by weight of cyclohexanone and 27% by weight of emulsifier, and diluted with water to the desired concentration.

Activity against Erysiphe graminis var. tritici (powdery mildew of wheat)

Leaves of wheat seedlings (cv. "Frühgold") were initially treated with the aqueous preparation of the active ingredients. After about 24 hours, the plants were dusted with spores of powdery mildew of wheat (*Erysiphe graminis* var. tritici). The thus-treated plants were subsequently incubated at 20–22° C. and a relative atmospheric humidity of 75–80% for 7 days. The extent of the fungal development was then determined.

Evaluation was carried out by determining the infected leaf areas in percent. These percentages were converted into efficacies. The efficacy (E) was calculated as follows using Abbot's formula:

$$E=(1-\alpha)\cdot 100/\beta$$

α corresponds to the fungal infection of the treated plants in % and

β corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the mixtures of the active ingredients were determined using Colby's formula [R. S. Colby, Weeds 15, 20–22 (1967)] and compared with the observed efficacies.

$$\text{Colby's formula: } E=x+y-x\cdot y/100$$

E expected efficacy, expressed in % of the untreated control, when using the mixture, disclosed in DE Appl. 19617232.2, of the active ingredients I and II (=active ingredient mixture A) and the active ingredients III at the concentrations a and c x efficacy, expressed in % of the untreated control, when using a mixture, disclosed in DE Appl. 19617232.2, of the active ingredients I and II at a concentration of a y efficacy, expressed in % of the untreated control, when using active ingredient III at a concentration of c

Use Example 1

Activity against powdery mildew of wheat

Leaves of wheat seedlings cv. "Frühgold" which had been grown in pots were sprayed to runoff point with an aqueous preparation of active ingredient which had been prepared from a stock solution comprising 10% of active ingredient, 63% of cyclohexanone and 27% of emulsifier and, 24 hours after the spraycoating had dried on, dusted with spores of powdery mildew of wheat (Erysiphe graminis forma specialis tritici). The test plants were subsequently placed in a greenhouse at from 20 to 24° C. and a relative atmospheric humidity of 60 to 90%. After 7 days, the extent of mildew development was determined visually as percent infection of the total leaf area.

The visually determined values for the percentage of infected leaf area were converted into efficacies as percent of the untreated control. Efficacy 0 means the same disease level as in the untreated control, efficacy 100 means 0% disease. The expected efficacies for active ingredient combinations were determined using Colby's formula (Colby, S. R. "Calculating synergistic and antagonistic responses of herbicide combinations", Weeds, 15, p. 20–22, 1967) and compared with the observed efficacies.

| Active ingredient | Concentration of active ingredient in the spray liquor in ppm | Efficacy in % of the untreated control |
|---|---|---|
| Control (untreated) | (98% diseased) | 0 |
| Ia.32 + II.a known from DE Appl. No. 19617232.2 | 1.25 + 1.25<br>0.31 + 0.31 | 0<br>0 |

-continued

| | | |
|---|---|---|
| Ia.32 + II.b | 1.25 + 1.25 | 8 |
| known from DE Appl. No. 19617232.2 | 0.31 + 0.31 | 0 |
| Ia.38 + II.a | 1.25 + 1.25 | 0 |
| known from DE Appl. No. 19617232.2 | 0.31 + 0.31 | 0 |
| Ia.38 + II.b | 1.25 + 1.25 | 0 |
| known from DE Appl. No. 19617232.2 | 0.31 + 0.31 | 0 |
| I.b + II.a | 0.31 + 0.31 | 59 |
| known from DE Appl. No. 19617232.2 | | |
| I.b + II.b | 0.31 + 0.31 | 59 |
| known from DE Appl.No. 19617232.2 | | |
| III.23 | 1.25 | 0 |
| known from DE Appl. No. 19617232.2 | 0.31 | 0 |
| III.24 | 1.25 | 8 |
| known from DE Appl. No. 19617232.2 | 0.31 | 8 |
| III.27 | 1.25 | 39 |
| known from DE Appl. No. 19617232.2 | 0.31 | 8 |

| Mixtures | Observed efficacy | Calculated efficacy*) |
|---|---|---|
| [Ia.32 + II.a 1.25 + 1.25 ppm] + III.23 1.25 ppm mixture 1:1:1 | 38 | 0 |
| [Ia.32 + II.a 0.31 + 0.31 ppm] + III.23 0.31 ppm mixture 1:1:1 | 28 | 0 |
| [Ia.32 + II.a 1.25 + 1.25 ppm] + III.24 1.25 ppm mixture 1:1:1 | 93 | 8 |
| [Ia.32 + II.a 0.31 + 0.31 ppm] + III.24 0.31 ppm mixture 1:1:1 | 39 | 8 |
| [Ia.32 + II.a 1.25 + 1.25 ppm] + III.27 1.25 ppm mixture 1:1:1 | 59 | 39 |
| [Ia.32 + II.a 0.31 + 0.31 ppm] + III.27 0.31 ppm mixture 1:1:1 | 39 | 8 |
| [Ia.32 + II.b 1.25 + 1.25 ppm] + III.23 1.25 ppm mixture 1:1:1 | 39 | 8 |
| [Ia.32 + II.b 0.31 + 0.31 ppm] + III.23 0.31 ppm mixture 1:1:1 | 28 | 0 |
| [Ia.32 + II.b 1.25 + 1.25 ppm] + III.24 1.25 ppm mixture 1:1:1 | 90 | 16 |
| [Ia.32 + II.b 0.31 + 0.31 ppm] + III.24 0.31 ppm mixture 1:1:1 | 39 | 8 |
| [Ia.32 + II.b 1.25 + 1.25 ppm] + III.27 1.25 ppm mixture 1:1:1 | 85 | 44 |
| [Ia.32 + II.b 0.31 + 0.31 ppm] + III.27 0.31 ppm mixture 1:1:1 | 39 | 8 |
| [Ia.38 + II.a 1.25 + 1.25 ppm] + III.23 1.25 ppm mixture 1:1:1 | 39 | 0 |
| [Ia.38 + II.a 0.31 + 0.31 ppm] + III.23 0.31 ppm mixture 1:1:1 | 29 | 0 |
| [Ia.38 + II.a 1.25 + 1.25 ppm] + III.24 1.25 ppm mixture 1:1:1 | 29 | 8 |
| [Ia.38 + II.a 0.31 + 0.31 ppm] + III.24 0.31 ppm mixture 1:1:1 | 29 | 8 |
| [Ia.38 + II.b 1.25 + 1.25 ppm] + III.23 1.25 ppm mixture 1:1:1 | 39 | 8 |
| [Ia.38 + II.b 0.31 + 0.31 ppm] + III.23 0.31 ppm mixture 1:1:1 | 28 | 0 |
| [Ia.38 + II.b 1.25 + 1.25 ppm] + III.24 1.25 ppm mixture 1:1:1 | 69 | 8 |
| [Ia.38 + II.b 0.31 + 0.31 ppm] + III.24 0.31 ppm mixture 1:1:1 | 39 | 8 |
| [Ia.38 + II.b 1.25 + 1.25 ppm] + III.27 1.25 ppm mixture 1:1:1 | 59 | 39 |
| [Ia.38 + II.b 0.31 + 0.31 ppm] + III.27 0.31 ppm mixture 1:1:1 | 29 | 8 |
| [I.b + II.a 0.31 + 0.31 ppm] + III.23 0.31 ppm mixture 1:1:1 | 85 | 59 |
| [I.b + II.a 0.31 + 0.31 ppm] + III.24 0.31 ppm | 89 | 63 |
| [I.b + II.a 0.31 + 0.31 ppm] + III.27 0.31 ppm | 85 | 63 |
| [I.b + II.b 0.31 + 0.31 ppm] + III.23 0.31 ppm | 95 | 59 |
| [I.b + II.b 0.31 + 0.31 ppm] + III.24 0.31 ppm | 90 | 63 |
| [I.b + II.b 0.31 + 0.31 ppm] + III.27 0.31 ppm | 85 | 63 |

*)calculated using Colby's formula

The test results show that the observed efficacy in all mixing ratios is higher than the efficacy that had been calculated beforehand using Colby's formula.

Use Example 2

Curative action against Puccinia recondita on wheat (brown rust of wheat)

Leaves of wheat seedlings cv. "Frühgold" which had been grown in pots were dusted with spores of brown rust (Puccinia recondita). The pots were then kept for 24 hours in a chamber of high atmospheric humidity (90 to 95%) at 20 to 22° C. During this time, the spores germinated and the germinal tubes penetrated into the leaf tissue. The next day, the infected plants were sprayed to runoff point with an aqueous preparation of active ingredient which had been prepared from a stock solution comprising 10% of active ingredient, 63% of cyclohexanone and 27% of emulsifier. After the spray coating had dried on, the test plants were cultivated in a greenhouse at temperatures from 20 to 22° C. and at 65 to 70% relative atmospheric humidity for 7 days. The extent of the rust fungus development on the leaves was then determined.

The visually determined values for the percentage of infected leaf area were converted into efficacies as percent of the untreated control. Efficacy 0 means the same disease level as in the untreated control, efficacy 100 means 0% disease. The expected efficacies for active ingredient combinations were determined using Colby's formula (Colby, S. R. "Calculating synergistic and antagonistic responses of herbicide combinations", Weeds, 15, p. 20–22, 1967) and compared with the observed efficacies.

| Active ingredient | Concentration of active ingredient in the spray liquor in ppm | Efficacy in % of the untreated control |
|---|---|---|
| Control (untreated) | (100% diseased) | 0 |
| Ia.32 + II.a | 1.25 + 1.25 | 60 |
| known from DE Appl. No. 19617232.2 | 0.31 + 0.31 | 0 |
| Ia.32 + II.b | 1.25 + 1.25 | 0 |
| known from DE Appl. No. 19617232.2 | 0.31 + 0.31 | 0 |
| Ia.38 + II.a | 1.25 + 1.25 | 20 |
| known from DE Appl. No. 19617232.2 | 0.31 + 0.31 | 0 |
| Ia.38 + II.b | 1.25 + 1.25 | 20 |
| known from DE Appl. No. 19617232.2 | 0.31 + 0.31 | 0 |
| I.b + II.a | 1.25 + 1.25 | 0 |
| known from DE Appl. No. 19617232.2 | 0.31 + 0.31 | 0 |
| I.b + II.b | 0.31 + 0.31 | 0 |
| known from DE Appl. No. 19617232.2 | | |
| III.8 | 0.31 | 0 |
| III.12 | 1.25 | 0 |
| | 0.31 | 0 |
| III.23 | 1.25 | 0 |
| | 0.31 | 0 |
| III.24 | 1.25 | 0 |
| | 0.31 | 0 |
| III.27 | 1.25 | 0 |
| | 0.31 | 0 |

| Mixtures | Observed efficacy | Calculated efficacy* |
|---|---|---|
| [Ia.32 + II.a 0.31 + 0.31 ppm] + III.8 0.31 ppm mixture 1:1:1 | 60 | 0 |
| [Ia.32 + II.a 1.25 + 1.25 ppm] + III.12 1.25 ppm mixture 1:1:1 | 85 | 60 |
| [Ia.32 + II.a 0.31 + 0.31 ppm] + III.12 0.31 ppm mixture 1:1:1 | 30 | 0 |
| [Ia.32 + II.a 0.31 + 0.31 ppm] + III.23 0.31 ppm mixture 1:1:1 | 40 | 0 |
| [Ia.32 + II.a 0.31 + 0.31 ppm] + III.24 0.31 ppm mixture 1:1:1 | 30 | 0 |
| [Ia.32 + II.b 0.31 + 0.31 ppm] + III.8 0.31 ppm mixture 1:1:1 | 40 | 0 |
| [Ia.32 + II.b 1.25 + 1.25 ppm] + III.12 1.25 ppm mixture 1:1:1 | 70 | 0 |
| [Ia.32 + II.b 0.31 + 0.31 ppm] + III.12 0.31 ppm mixture 1:1:1 | 30 | 0 |
| [Ia.32 + II.b 1.25 + 1.25 ppm] + III.23 1.25 ppm mixture 1:1:1 | 30 | 0 |
| [Ia.32 + II.b 1.25 + 1.25 ppm] + III.24 1.25 ppm mixture 1:1:1 | 25 | 0 |
| [Ia.32 + II.b 0.31 + 0.31 ppm] + III.27 0.31 ppm mixture 1:1:1 | 30 | 0 |
| [Ia.38 + II.a 0.31 + 0.31 ppm] + III.8 0.31 ppm mixture 1:1:1 | 40 | 0 |
| [Ia.38 + II.a 1.25 + 1.25 ppm] + III.12 1.25 ppm mixture 1:1:1 | 50 | 20 |
| [Ia.38 + II.a 0.31 + 0.31 ppm] + III.23 0.31 ppm mixture 1:1:1 | 20 | 0 |
| [Ia.38 + II.a 0.31 + 0.31 ppm] + III.24 0.31 ppm mixture 1:1:1 | 30 | 0 |
| [Ia.38 + II.a 1.25 + 1.25 ppm] + III.27 1.25 ppm mixture 1:1:1 | 85 | 20 |
| [Ia.38 + II.a 0.31 + 0.31 ppm] + III.27 0.31 ppm mixture 1:1:1 | 30 | 0 |
| [Ia.38 + II.b 0.31 + 0.31 ppm] + III.8 0.31 ppm mixture 1:1:1 | 50 | 0 |
| [Ia.38 + II.b 1.25 + 1.25 ppm] + III.27 1.25 ppm mixture 1:1:1 | 80 | 20 |
| [Ia.38 + II.b 0.31 + 0.31 ppm] + III.27 0.31 ppm mixture 1:1:1 | 30 | 0 |
| [I.b + II.a 0.31 + 0.31 ppm] + III.8 0.31 ppm mixture 1:1:1 | 50 | 0 |
| [I.b + II.a 0.31 + 0.31 ppm] + III.12 0.31 ppm mixture 1:1:1 | 40 | 0 |
| [I.b + II.a 1.25 + 1.25 ppm] + III.23 1.25 ppm mixture 1:1:1 | 30 | 0 |
| [I.b + II.a 0.31 + 0.31 ppm] + III.23 0.31 ppm mixture 1:1:1 | 20 | 0 |
| [I.b + II.a 1.25 + 1.25 ppm] + III.27 1.25 ppm mixture 1:1:1 | 80 | 0 |
| [I.b + II.b 0.31 + 0.31 ppm] + III.8 0.31 ppm | 75 | 10 |

*)calculated using Colby's formula

The test results show that the observed efficacy in all mixing ratios is higher than the efficacy that had been calculated beforehand using Colby's formula.

We claim:
1. A fungicidal composition comprising synergistically effective amounts of
a) a first active component I selected from the group consisting of
a.1) carbamates of formula I.a,

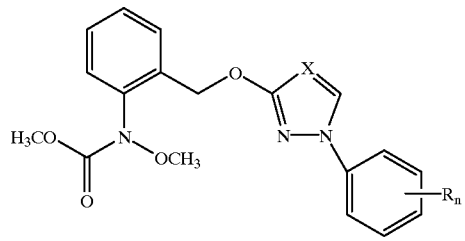

I.a wherein X is CH or N, n is 0, 1 or 2 and R is halogen, $C_1$–$C_4$-alkyl or $C_1$–$C_4$-haloalkyl, where the radicals R are identical or different when n is 2, and salts and adducts thereof, and
a.2) an oxime ether carboxamide of formula I.b

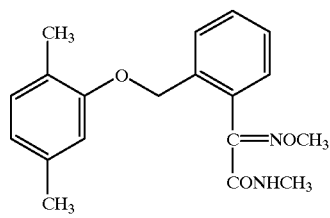

I.b and
b) a second active component II selected from the group consisting of
b.1) 4-[2-methyl-3-(4-tert-butylphenyl)propyl]-2,6-dimethyl-morpholine

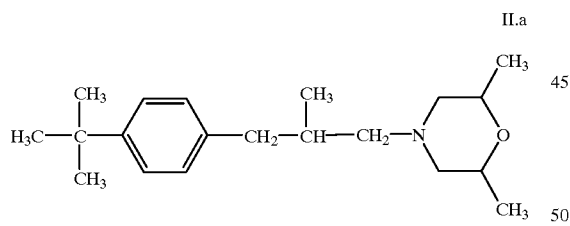

II.a b.2) 4-($C_{10}$–$C_{13}$-alkyl)-2,6-dimethylmorpholine

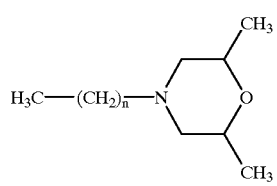

II.b

[n = 10, 11, 12 (60–70%), 13]

and
b.3)(RS)-1-[3-(4-tert-butylphenyl)-2-methylpropyl]-piperidine

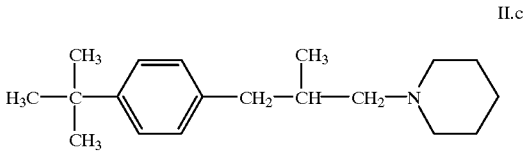

II.c and
c) a third active component III selected from the group of azole fungicides.

2. The composition defined in claim 1, wherein the active component III is selected from the group consisting of III.1  1-[2-(2,4-dichlorophenyl)-1,3-dioxolan-2-yl]-1H-1,2,4-triazole

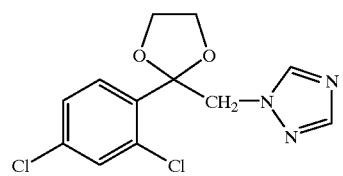

III.1

III.2  1-(biphenyl-4-yloxy)-3,3-dimethyl-1-(1H-1,2,4-triazol-1-yl)butan-2-ol

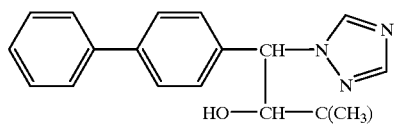

III.2

III.3  1-[(2RS, 4RS; 2RS, 4SR)-4-bromo-2-(2,4-dichlorophenyl)tetrahydrofurfuryl]-1H-1,2,4-triazole

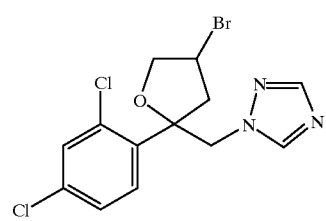

III.3

III.4  (2RS,3RS,2RS,3SR)-2-(4-chlorophenyl)-3-cyclopropyl-1-(1H-1,2,4-triazol-1-yl)butan-2-ol

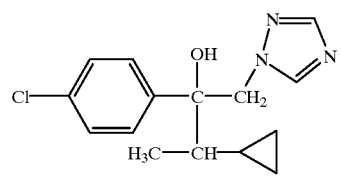

III.4

III.5  (2RS,3RS)-1-(2,4-dichlorophenyl)-4,4-dimethyl-2-(1H-1,2,4-triazol-1-yl)pentan-3-ol

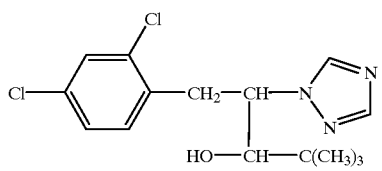

III.6 cis,trans-3-chloro-4-[4-methyl-2-(1H-1,2,4-triazol-1-ylmethyl)-1,3-dioxolan-2-yl]-phenyl 4-chlorophenyl ether

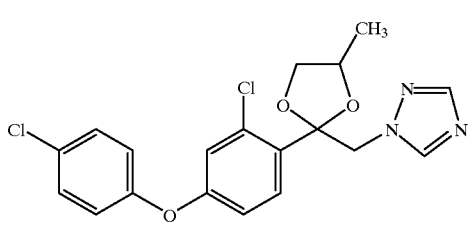

III.7 (E)-(R,S)-1-(2,4-dichlorophenyl)-4,4-dimethyl-2-(1H-1,2,4-triazol-1-yl)pent-1-en-3-ol III.8 (2RS,3RS)-1-[3-(2-chlorophenyl)-2,3-epoxy-2-(4-fluorophenyl)propyl]-1H-1,2,4-triazole

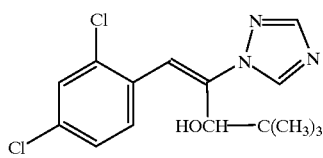

III.9 (±)-1-[2-(2,4-dichlorophenyl)-4-ethyl-1,3-dioxolan-2-ylmethyl]-1H-1,2,4-triazole

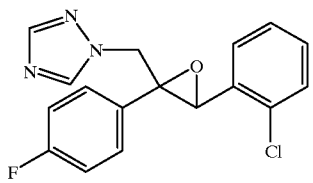

III.10 (RS)-4-(4-chlorophenyl)-2-phenyl-2-(1H-1,2,4-triazol-1-ylmethyl)butyronitrile

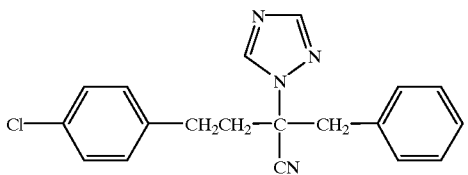

III.11 3-(2,4-dichlorophenyl)-6-fluoro-2-(1H-1,2,4-triazol-1-yl)quinazolin-4(3H)-one

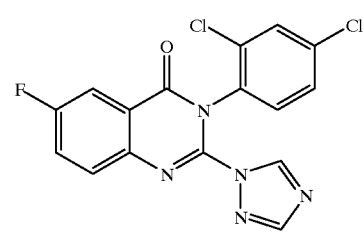

III.12 bis-(4-fluorophenyl)(methyl)-(1H-1,2,4-triazol-1-ylmethyl)silane

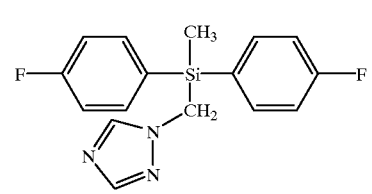

III.13 (RS)-2,4'-difluoro-α-(1H-1,2,4-triazol-1-ylmethyl) benzhydryl alcohol

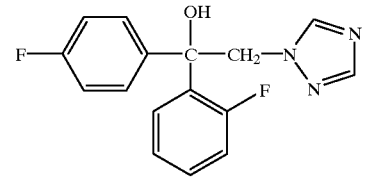

III.14 (RS)-2-(2,4-dichlorophenyl)-1-(1H-1,2,4-trlazol-1-yl)hexan-2-ol

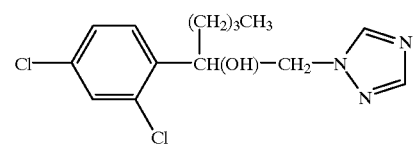

III.15 (±)-1-(β-allyloxy-2,4-dichlorophenylethyl) imidazole

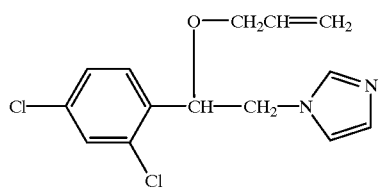

III.16 4-chlorobenzyl N-(2,4-dichlorophenyl)-2-(1H-1,2,4-triazol-1-yl)thioacetamidate

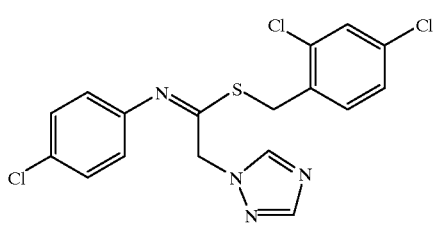

III.17 (1RS,2SR,5RS;1RS,2SR,5SR)-2-(4-chlorobenzyl)-5-isopropyl-1-(1H-1,2,4-triazol-1-ylmethyl)cyclopentanol

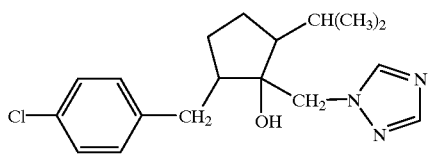

III.18 (1RS,5RS;1RS,5SR)-5-(4-chlorobenzyl)-2,2-dimethyl-1-(1H-1,2,4-triazol-1-ylmethyl)cyclopentanol

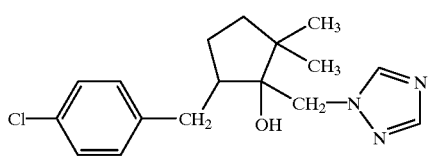

III.19 2-(4-chlorophenyl)-2-cyano-1-(1H-1,2,4-triazol-1-yl)hexane

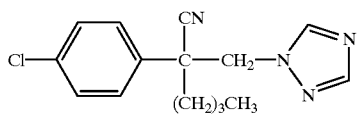

III.20 2-(4-chlorophenyl)-3-hydroxy-4,4-dimethyl-1-(1H-1,2,4-triazol-1-yl)pentane

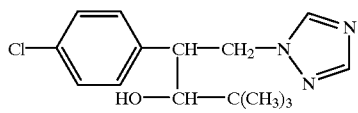

III.21 pent-4-enyl N-furfuryl-N-imidazol-1-ylcarbonyl-DL-homoalaninate

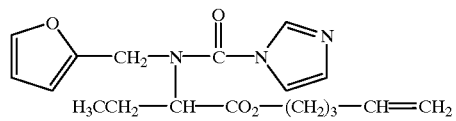
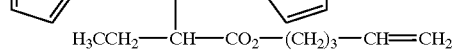

III.22 2-(2,4-dichlorophenyl)-1-(1H-1,2,3-triazol-1-yl)pentane

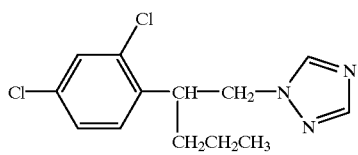

III.23 N-propyl-N-[(2,4,6-trichlorophenoxy)ethyl]imidazole-1-carboxamide

III.24 (±)-1-{[2-(2,4-dichlorophenyl)-4-propyl-1,3-dioxolan-2-yl]methyl}-1H-1,2,4-triazole III.25 3-(2,4-dichlorophenyl)-2-(1H-1,2,4-triazol-1-yl)quinazolin-4(3H)-one

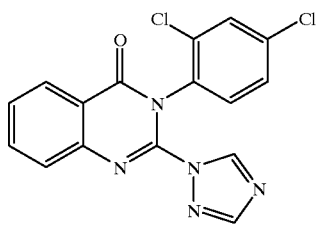

III.25

III.26 (±)-cis-1-(4-chlorophenyl)-2-(1H-1,2,4-triazol-1-yl)cycloheptanol

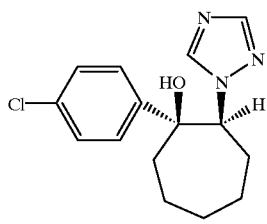

III.26

III.27 1-(4-chlorophenyl)-4,4-dimethyl-3-(1H-1,2,4-triazol-1-yl)pentan-3-ol

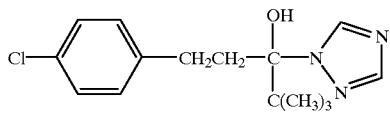

III.27

III.28 (RS)-2-(2,4-dichlorophenyl)-3-(1H-1,2,4-triazol-1-yl)propyl 1,1,2,2-tetrafluoroethyl ether

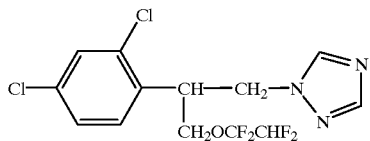

III.28

III.29 1-(4-chlorophenoxy)-3,3-dimethyl-1-(1H-1,2,4-triazol-1-yl)butan-2-one

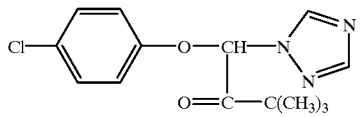

III.29

III.30 (1RS,2RS;1RS,2SR)-1-(4-chlorophenoxy)-3,3-dimethyl-1-(1H-1,2,4-triazol-1-yl)butan-2-ol

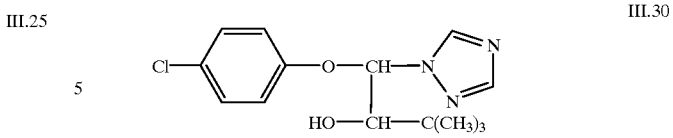

III.30

III.31 (E)-4-chloro-α,α,α-trifluoro-N-(1-imidazol-1-yl-2-propoxyethylidene)-o-toluidine

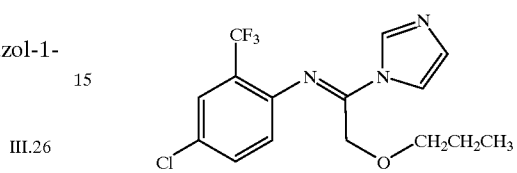

III.31

III.32 (±)-(E)-5-(4-chlorobenzylidene)-2,2-dimethyl-1-(1H-1,2,4-triazol-1-ylmethyl)cyclopentanol

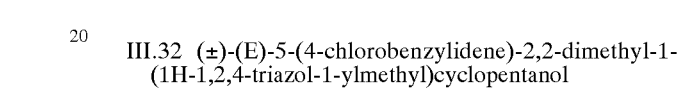

III.32 and
III.33 (E)-(RS)-1-(4-chlorophenyl)-4,4-dimethyl-2-(1H-1,2,4-triazol-1-yl)pent-1-en-3-ol.

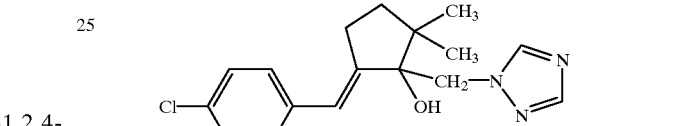

III.33

3. The composition defined in claim 1, wherein the active component I and the active component II are present in a weight ratio of from 10:1 to 0.01:1.

4. The composition defined in claim 1, wherein the active component I and the active component III are present in a weight ratio of from 10:1 to 0.01:1.

5. The composition defined in claim 1, which is conditioned in two parts, one part comprising the active component I in a solid or liquid carrier, and the other part comprising the active component II in a solid or liquid carrier, and one of the two parts additionally comprising the active component III.

6. The composition defined in claim 1 which is conditioned in three parts, the first part comprising the active component I in a solid or liquid carrier, the second part comprising the active component II in a solid or liquid carrier, and the third part comprising the active component III in a solid or liquid carrier.

7. The composition defined in claim 1, wherein the active component I comprises a carbamate of formula I.a or an adduct or salt thereof.

8. The composition defined in claim 7, wherein the active component I and the active component II are present in a weight ratio of from 10:1 to 0.01:1.

9. The composition defined in claim 7, wherein the active component I and the active component III are present in a weight ratio of from 10:1 to 0.01:1.

10. The composition defined in claim 7, which is conditioned in two parts, one part comprising the active component I in a solid or liquid carrier, and the other part comprising the active component II in a solid or liquid carrier, and one of the two parts additionally comprising the active component III.

11. The composition defined in claim 7 which is conditioned in three parts, the first part comprising the active component I in a solid or liquid carrier, the second part comprising the active component II in a solid or liquid carrier, and the third part comprising the active component III in a solid or liquid carrier.

12. A method for controlling harmful fungi, which comprises treating the harmful fungi, their habitat, or plants, seeds, soils, areas, materials or spaces to be kept free from said fungi with synergistically effective amounts of an active component I, an active component II, and an active component III, wherein the active components I to III are as set forth in claim 1.

13. The method of claim 12, wherein the active component I, the active component II, and the active component III are applied simultaneously, that is either together or separately, or in succession.

14. The method of claim 12, wherein the active component I is applied in an amount of from 0.01 to 2.5 kg/ha.

15. The method of claim 12, wherein the active component II is applied in an amount of from 0.01 to 10 kg/ha.

16. The method of claim 12, wherein the active component III is applied in an amount of from 0.01 to 10 kg/ha.

17. The method of claim 12, wherein the active component I comprises a carbamate of formula I.a or an adduct or salt thereof.

18. The method of claim 17, wherein the active component I is applied in an amount of from 0.01 to 2.5 kg/ha.

19. The method of claim 17, wherein the active component II is applied in an amount of from 0.01 to 10 kg/ha.

20. The method of claim 17, wherein the active component III is applied in an amount of from 0.01 to 10 kg/ha.

* * * * *